United States Patent [19]
Aboul-Hosn

[11] Patent Number: 6,123,725
[45] Date of Patent: Sep. 26, 2000

[54] SINGLE PORT CARDIAC SUPPORT APPARATUS

[75] Inventor: Walid N. Aboul-Hosn, Sacramento, Calif.

[73] Assignee: A-Med Systems, Inc., Sacramento, Calif.

[21] Appl. No.: 08/891,456

[22] Filed: Jul. 11, 1997

[51] Int. Cl.$^7$ .................................................. A61M 1/10
[52] U.S. Cl. ......................... 623/3.25; 623/3.26; 604/43; 604/284
[58] Field of Search .................................. 623/1, 11, 12, 623/3, 3.25, 3.26; 606/191, 194, 195, 198; 604/4, 43, 284

[56] References Cited

U.S. PATENT DOCUMENTS

| | | | |
|---|---|---|---|
| Re. 28,742 | 3/1976 | Rafferty et al. | 415/90 |
| 2,669,668 | 2/1954 | Okulitch et al. | 310/104 |
| 3,487,784 | 1/1970 | Rafferty et al. . | |
| 3,608,088 | 9/1971 | Dorman et al. | 3/1 |
| 3,626,947 | 12/1971 | Sparks | 623/1 |
| 3,647,324 | 3/1972 | Rafferty et al. | 417/420 |
| 3,771,527 | 11/1973 | Ruisi | 604/43 |
| 3,864,055 | 2/1975 | Kletschka et al. | 415/1 |
| 3,896,501 | 7/1975 | Bifano et al. | 3/1.7 |
| 3,957,389 | 5/1976 | Rafferty et al. | 415/1 |

(List continued on next page.)

FOREIGN PATENT DOCUMENTS

| | | |
|---|---|---|
| 1 222 355 | 6/1987 | Canada . |
| 1 240 802 | 8/1988 | Canada . |
| 1 302 829 | 6/1992 | Canada . |
| 1 308 319 | 10/1992 | Canada . |
| 1 323 467 | 10/1993 | Canada . |
| 1 328 708 | 4/1994 | Canada . |
| 280 225 | 8/1988 | European Pat. Off. . |
| 0157871 B1 | 7/1990 | European Pat. Off. . |
| 0445782 A1 | 9/1991 | European Pat. Off. . |

(List continued on next page.)

OTHER PUBLICATIONS

Allaire, P.E., et al., "Prototype Continuous Flow Ventricular Assist Device Supported on Magnetic Bearings", Artificial Organs, vol. 20, No. 6, pp. 582–590, 1996.

Anai, Hirofumi, et al., "Relationship Between Pump Speed Design and Hemolysis in an Axial Flow Blood Pump", Artificial Organs, vol. 20, No. 6, pp. 564–567, 1996.

Andrade, Aron, et al., "Characteristics of a Blood Pump Combining the Centrifugal and Axial Pumping Principles: The Spiral Pump", Artificial Organs, vol. 20, No. 6, pp. 605–612, 1996.

Burgreen, Greg W, et al., "A design Improvement Strategy for Axial Blood Pumps Using Computational Fluid Dynamics", ASAIO Journal; 42:M354–M360, 1996.

(List continued on next page.)

*Primary Examiner*—Michael J. Milano
*Assistant Examiner*—Tram A. Nguyen
*Attorney, Agent, or Firm*—Jonathan Spangler

[57] ABSTRACT

A reverse flow pump comprising two concentric passageways and an interior compartment having cut out portions in communication with a pump passageway for the directional flow of fluid relative to the pump, and a rotor positioned within the interior compartment for reversing the directional flow of fluid through a region in communication with another pump passageway. A reverse flow pump and cannula system is further provided comprising an inner cannula adjoining a pump passageway, and an outer conduit adjoining another pump passageway for the reverse flow of fluid relative to the pump. A method of transporting fluid between body cavities is also provided comprising the steps of selecting a reverse flow pump and cannula system, forming an opening in a body passageway, positioning the outer conduit through the opening, inserting the inner cannula into the outer conduit so that the distal openings of the inner cannula and the outer conduit are positioned in separated portions of the body, connecting the inlet and the outlet passageways of the pump to the proximal ends of the inner cannula and the outer conduit, and activating the pump to transport fluid between the separated portions of the body.

19 Claims, 5 Drawing Sheets

U.S. PATENT DOCUMENTS

| | | | |
|---|---|---|---|
| 3,970,408 | 7/1976 | Rafferty et al. | 415/60 |
| 3,995,617 | 12/1976 | Watkins et al. . | |
| 4,086,665 | 5/1978 | Poirier | 623/1 |
| 4,105,016 | 8/1978 | Donovan, Jr. | 128/1 |
| 4,108,161 | 8/1978 | Samuels et al. | 623/1 |
| 4,116,589 | 9/1978 | Rishton . | |
| 4,118,806 | 10/1978 | Porier et al. | 623/1 |
| 4,129,129 | 12/1978 | Amrine . | |
| 4,135,253 | 1/1979 | Reich et al. | 3/1.7 |
| 4,173,796 | 11/1979 | Jarvik . | |
| 4,275,988 | 6/1981 | Kalasknikov et al. . | |
| 4,382,199 | 5/1983 | Isaacson . | |
| 4,403,983 | 9/1983 | Edelman et al. | 604/43 |
| 4,451,252 | 5/1984 | Martin | 604/43 |
| 4,507,048 | 3/1985 | Belenger et al. | 415/90 |
| 4,512,726 | 4/1985 | Strimling | 417/412 |
| 4,567,882 | 2/1986 | Heller . | |
| 4,589,822 | 5/1986 | Clausen et al. | 415/170 |
| 4,606,698 | 8/1986 | Clausen et al. | 415/170 |
| 4,625,712 | 12/1986 | Wampler . | |
| 4,648,865 | 3/1987 | Aigner | 604/43 |
| 4,688,998 | 8/1987 | Olsen et al. . | |
| 4,704,121 | 11/1987 | Moise . | |
| 4,705,501 | 11/1987 | Wigness et al. | 604/43 |
| 4,753,221 | 6/1988 | Kensey et al. . | |
| 4,769,031 | 9/1988 | McGough et al. | 623/1 |
| 4,779,614 | 10/1988 | Moise . | |
| 4,817,586 | 4/1989 | Wampler . | |
| 4,844,707 | 7/1989 | Kletschka | 417/420 |
| 4,846,152 | 7/1989 | Wampler et al. . | |
| 4,895,557 | 1/1990 | Moise et al. . | |
| 4,898,518 | 2/1990 | Hubbard et al. | 417/360 |
| 4,906,229 | 3/1990 | Wampler . | |
| 4,908,012 | 3/1990 | Moise et al. . | |
| 4,919,647 | 4/1990 | Nash . | |
| 4,925,377 | 5/1990 | Inacio et al. . | |
| 4,927,407 | 5/1990 | Dorman | 600/16 |
| 4,944,722 | 7/1990 | Carriker et al. . | |
| 4,950,259 | 8/1990 | Geary et al. | 604/43 |
| 4,955,861 | 9/1990 | Energren et al. | 604/141 |
| 4,957,504 | 9/1990 | Chardack . | |
| 4,969,865 | 11/1990 | Hwang et al. . | |
| 4,984,972 | 1/1991 | Clausen et al. | 417/420 |
| 4,985,014 | 1/1991 | Orejola . | |
| 4,994,017 | 2/1991 | Yozu . | |
| 4,994,078 | 2/1991 | Jarvik . | |
| 4,995,857 | 2/1991 | Arnold . | |
| 5,009,636 | 4/1991 | Wortley et al. . | |
| 5,011,380 | 4/1991 | Kovacs | 417/413 |
| 5,019,102 | 5/1991 | Hoene | 623/2 |
| 5,044,369 | 9/1991 | Sahota | 606/194 |
| 5,044,897 | 9/1991 | Dorman . | |
| 5,049,134 | 9/1991 | Golding et al. | 604/151 |
| 5,053,004 | 10/1991 | Markel et al. | 604/43 |
| 5,055,005 | 10/1991 | Kletschka | 417/356 |
| 5,061,256 | 10/1991 | Wampler . | |
| 5,078,741 | 1/1992 | Bramm et al. . | |
| 5,079,467 | 1/1992 | Dorman | 310/156 |
| 5,092,844 | 3/1992 | Schwartz et al. . | |
| 5,092,879 | 3/1992 | Jarvik . | |
| 5,098,256 | 3/1992 | Smith | 415/111 |
| 5,112,200 | 5/1992 | Isaacson et al. . | |
| 5,112,202 | 5/1992 | Oshima et al. | 417/423 |
| 5,112,292 | 5/1992 | Hwang et al. . | |
| 5,118,264 | 6/1992 | Smith | 417/423.11 |
| 5,145,333 | 9/1992 | Smith | 417/405 |
| 5,147,187 | 9/1992 | Ito et al. | 417/423.1 |
| 5,147,388 | 9/1992 | Yamazaki . | |
| 5,167,223 | 12/1992 | Koros et al. . | |
| 5,167,623 | 12/1992 | Cianci et al. | 604/43 |
| 5,174,726 | 12/1992 | Findlay | 417/205 |
| 5,195,877 | 3/1993 | Kletschka | 417/356 |
| 5,205,721 | 4/1993 | Isaacson . | |
| 5,209,650 | 5/1993 | Lemieux . | |
| 5,234,456 | 8/1993 | Silvestrini . | |
| 5,275,580 | 1/1994 | Yamazaki . | |
| 5,282,849 | 2/1994 | Kolff et al. . | |
| 5,290,227 | 3/1994 | Pasque . | |
| 5,295,958 | 3/1994 | Shturman | 606/194 |
| 5,324,177 | 6/1994 | Golding et al. | 417/423.1 |
| 5,326,344 | 7/1994 | Bramm et al. . | |
| 5,344,443 | 9/1994 | Palma et al. . | |
| 5,360,317 | 11/1994 | Clausen et al. | 415/206 |
| 5,368,438 | 11/1994 | Raible . | |
| 5,370,509 | 12/1994 | Golding et al. | 417/423.1 |
| 5,370,610 | 12/1994 | Reynolds | 604/43 |
| 5,376,114 | 12/1994 | Jarvik . | |
| 5,380,276 | 1/1995 | Miller et al. | 604/43 |
| 5,385,581 | 1/1995 | Bramm et al. . | |
| 5,393,207 | 2/1995 | Maher et al. . | |
| 5,399,074 | 3/1995 | Nose et al. | 417/423.1 |
| 5,399,145 | 3/1995 | Ito et al. | 600/16 |
| 5,441,535 | 8/1995 | Takahashi et al. | 623/3 |
| 5,443,503 | 8/1995 | Yamane | 623/3 |
| 5,456,667 | 10/1995 | Ham et al. . | |
| 5,470,208 | 11/1995 | Kletschka | 417/356 |
| 5,478,309 | 12/1995 | Sweezer et al. . | |
| 5,480,380 | 1/1996 | Martin | 604/43 |
| 5,503,615 | 4/1996 | Goldstein | 600/16 |
| 5,507,629 | 4/1996 | Jarvik . | |
| 5,527,159 | 6/1996 | Bozeman, Jr. et al. . | |
| 5,531,789 | 7/1996 | Yamazaki et al. . | |
| 5,558,634 | 9/1996 | Mitchell | 604/43 |
| 5,575,630 | 11/1996 | Nakazawa et al. | 417/420 |
| 5,588,812 | 12/1996 | Taylor et al. . | |
| 5,613,935 | 3/1997 | Jarvik . | |
| 5,647,358 | 7/1997 | Vilasi | 623/11 |
| 5,695,471 | 12/1997 | Wampler . | |
| 5,707,218 | 1/1998 | Maher et al. . | |
| 5,727,569 | 3/1998 | Benetti et al. . | |
| 5,765,568 | 6/1998 | Sweezer, Jr. et al. . | |
| 5,766,209 | 6/1998 | Devonec | 623/12 |
| 5,782,797 | 7/1998 | Schweich, Jr. et al. . | |
| 5,800,375 | 9/1998 | Sweezer et al. . | |
| 5,810,757 | 9/1998 | Sweezer, Jr. et al. . | |
| 5,976,103 | 11/1999 | Martin | 604/43 |

FOREIGN PATENT DOCUMENTS

| | | |
|---|---|---|
| 0157859 B1 | 4/1992 | European Pat. Off. . |
| 0396575 B1 | 3/1994 | European Pat. Off. . |
| 0397668 B1 | 3/1994 | European Pat. Off. . |
| 0611580 A2 | 8/1994 | European Pat. Off. . |
| 0478635 B1 | 12/1994 | European Pat. Off. . |
| 0629412 A2 | 12/1994 | European Pat. Off. . |
| 0397720 B1 | 3/1995 | European Pat. Off. . |
| 0659443 A1 | 6/1995 | European Pat. Off. . |
| 0591208 B1 | 11/1995 | European Pat. Off. . |
| 0699447 A1 | 3/1996 | European Pat. Off. . |
| 0611580 B1 | 12/1996 | European Pat. Off. . |
| 0 768 091 | 4/1997 | European Pat. Off. . |
| 2233 293 | 1/1973 | Germany . |
| 24 53 296 | 5/1976 | Germany . |
| 286 145 | 1/1971 | Russian Federation . |
| 545 358 | 7/1977 | Russian Federation . |
| WO 85/01432 | 4/1985 | WIPO . |
| WO 85/01436 | 4/1985 | WIPO . |
| WO 88/07842 | 10/1988 | WIPO . |
| WO 89/04644 | 6/1989 | WIPO . |
| WO 89/04645 | 6/1989 | WIPO . |
| WO 89/05668 | 6/1989 | WIPO . |
| WO 89/07427 | 8/1989 | WIPO . |
| WO 90/15640 | 12/1990 | WIPO . |

| | | |
|---|---|---|
| WO 91/01584 | 2/1991 | WIPO . |
| WO 92/02263 | 2/1992 | WIPO . |
| WO 92/03181 | 3/1992 | WIPO . |
| WO 92/06297 | 4/1992 | WIPO . |
| WO 93/07388 | 4/1993 | WIPO . |
| WO 93/20860 | 10/1993 | WIPO . |
| WO 94/06486 | 3/1994 | WIPO . |
| WO 94/09274 | 4/1994 | WIPO . |
| WO 94/09835 | 5/1994 | WIPO . |
| WO 94/13955 | 6/1994 | WIPO . |
| WO 95/00185 | 1/1995 | WIPO . |
| WO 95/28185 | 10/1995 | WIPO . |
| WO 96/18358 | 6/1996 | WIPO . |
| WO 97/40751 | 11/1997 | WIPO . |

OTHER PUBLICATIONS

Daily, Bill B., et al. "Pierce–Donarchy Pediatric VAD: Process in Development", Annals of Thoracic Surgery; 61:437–443, 1996.

Golding Leonard A. R., et al., "The Cleveland Clinic Rotodynamic Pump Program", Artificial Organs, vol. 20, No. 6, pp. 481–484, 1996.

Hart, Robert M., et al., "A Magnetically Suspended and Hydrostatically Stabilized Centrifugal Blood Pump", Artificial Organs, vol. 20, No. 6, pp. 591596, 1996.

Kaufmann, Ralf, et al., "The Implantable Fuzzy Controlled Helmholtz–Left Ventricular Assist Device: First in Vitro Testing," Artificial Organs, vol. 21, No. 2, pp. 131–137, 1997.

Kawahito, K., et al, "Ex Vivo Evaluation of the NASA/DeBakey Axial Flow Ventricular Assist Device", ASAIO Journal; 42:M754–M757, 1996.

Khanwilker, Pratap, et al., "Using Hybrid Magnetic Bearings to Completely suspend the Impeller of a Ventricular Assist Device", Artificial Organs, vol. 20, No. 6, pp. 597–604, 1996.

McCarthy, Patrick M., et al., "Permanent Mechanical Circulatory Support With an Implantable Left Ventricular Assist Device," Annals of Thoracic Surgery;63:1458–61, 1997.

Nishimura, Kazunobu, et al., "Developement of a Magnetically Suspended Centrifugal Pump as a Cardiac Assist Device for Long–Term Application", ASAIO Journal pp. 68–71, 1996.

Kubo, Hironao, " Marine Propellers: The Latest Topics," Artificial Organs, vol. 21, No. 2, pp. 109–113, 1996.

Nakazawa, Tadashi, et al., " The Development of Pivot Bearing Supported Sealless Centrifugal Pump for Ventricular Assist", Artificial Organs, vol. 20, No. 6, pp. 485–490, 1996.

Nakazawa, Tadashi, et al., " The Effect of the Impeller–Driver Magnetic Coupling Distance on Hemolysis in a Compact Centrifugal Pump" Artificial Organs, vol. 20, No. 3, pp. 252–257, 1996.

Rosenfeldt, Franklin L., et al., " A Novel Valveless Rotary Pump for Cardiac Assist", Artificial Organs, vol. 21, No. 5, pp. 420–425, 1997.

Takami, Yoshiyuki, et al., " Effect of Surface Roughness on Hemolysis in a Centrifugal Blood Pump", ASAIO Journal; vol. 42 pp. M858–M862.

Takami, Yoshiyuki, et al., " Effect of Surface Roughness on Hemolysis in a Pivot Bearing Supported Gyro Centrifugal Pump (C1E3)", Artificial Organs; vol. 20, No. 11 pp. 1155–1161, 1996.

Takami, Yoshiyuki, et al., "Material of the Double Pivot Bearing System in the Gyro C1E3 Centrifugal Pump", Artificial Organs; vol. 21, No. 2, pp. 143–147, 1997.

Takano, Hisateru, et al., "Ventricular Assist Systems: Experience in Japan with Toyobo Pump and Zeon Pump," Annals of Thoracic Surgery, 1996; 61:317–22.

Tsukiya, Tomonori, "Use of Motor Current in Flow Rate Measurement for the Magnetically Suspended Centrifugal Blood Pump", Artificial Organs, vol. 21, No. 5, pp. 396–401, 1997.

FIG.—6

SINGLE PORT CARDIAC SUPPORT APPARATUS

BACKGROUND OF THE INVENTION

1. Field of the Invention

The present invention relates generally to apparatus and method for providing cardiac support during cardiac surgery. More particularly, to such apparatus and method for providing cardiac support which are less traumatic and invasive.

2. Description of the Related Art

When it is necessary to perform cardiac surgery, surgery has heretofore been accomplished by major open heart surgical procedure, requiring general anaesthesia and full cardio-pulmonary bypass. Such surgery usually includes about three weeks of hospitalization and months of recuperation. Average mortality rate for this procedure is approximately 1% with complication rate being substantially higher. Descriptions of open heart procedure can be found in Gibbon's Surgery of the Chest 5th Edition, (David C. Sabiston, Jr., M.D., Frank D. Spencer, M.D. 1990, Vol. 11, Ch. 52, pp. 1, 56–61, 596, and Textbook of Interventional Cardiology, Eric J. Topol, 1990, Chs. 43–44, pp. 831–867).

Coronary artery bypass graft procedure is one type of open chest surgical technique used to treat coronary artery disease. During the procedure, the patient's sternum must be opened with the chest spread apart to provide access to the heart. The patient's blood is cooled and diverted from the patient's lung to an artificial oxygenator. A source of arterial blood is then connected to a coronary artery downstream from the occlusion while the patient undergoes cardiac arrest and is supported by cardiopulmonary bypass (CPB). The source of blood is often the left or right internal mammary artery and the target coronary artery is the anterior or posterior arteries which might be narrowed or occluded.

While very effective in many cases, the use of open chest surgery to perform CPB is very traumatic to the patient. The procedure requires immediate post-operative care in an intensive care unit. The total period for hospitalization may be seven to ten days, while the total recovery period that may be as long as six to eight weeks. In addition, open heart procedure requires the use of CPB which continues to represent a major assault on a host of body systems. For example, in up to 24% of the open chest coronary bypass surgeries performed in the United States, there is a noticeable degradation of the patient's mental faculties following such surgeries. This degradation is commonly attributed to cerebral arterial blockage from debris and emboli generated during the surgical procedure.

In addition, much post-operative morbidity, and some mortality, is attributed to the shortcomings of CPB.

SUMMARY OF THE INVENTION

It is an object of the present invention to provide an apparatus which provides cardiac support during cardiac surgery.

It is another object of the present invention to provide such an apparatus which is less traumatic and invasive to the patient than current apparatus used today.

It is a further object of the present invention to provide a method for providing cardiac support using the apparatus described herein.

These and other objects are met by providing an apparatus that is used extravascularly, possibly trans-valvularly, and requires only one incision into a major blood vessel, such as the aorta. The apparatus includes an elongated inner cannula which is inserted through a portal formed in a major blood vessel or heart chamber. Disposed coaxially over the inner cannula is an outer conduit. A reverse flow pumping means is disposed between the proximal openings on the inner cannula and outer conduit which pumps blood delivered by the inner cannula to the outer conduit. The distal openings on the inner cannula and outer conduit are spaced apart and disposed either in different blood vessels or transvalvularly in the heart so that blood flowing into the distal opening of the inner cannula may be delivered through the distal opening on the outer conduit located downstream or proximal from the distal opening of the inner cannula. For example in one embodiment described herein, a portal is formed in the aorta with the distal opening on the outer conduit extended therethrough. The inner cannula is positioned through the aortic valve and disposed inside the left ventricle. Blood delivered to the left ventricle is then pumped through the inner cannula via the pumping means and deposited in the aorta via the outer conduit, thus unloading the left ventricle. Optional balloons may be selectively inflated on the outside surface of the inner cannula or outer conduit which act to seal off the passageway between the sides of the blood vessel and the cannula, to cool adjacent tissue, or to deliver drugs to adjacent tissue.

Using the above described apparatus, a method of providing cardiac support is also provided.

Other objects and advantages of the present invention will become apparent from the following description of the preferred embodiments taken into conjunction with the accompanying drawings wherein like parts in each of the several figures are identified by the same reference characters.

DESCRIPTION OF THE PREFERRED EMBODIMENT(S)

Referring to the accompanying FIGS. 1–7, therein is shown a cardiac support apparatus, generally referred to as 10, designed to provide cardiac support during cardiac surgery.

The apparatus 10 includes coaxially aligned, inner cannula 20 and outer conduit 30 with a reverse flow pump 50 disposed between them designed to pump blood delivered by the inner cannula 20 to the outer conduit 30, and then throughout the body. By using such an arrangement, only one portal is required into a major blood vessel.

In the embodiments shown herein, the inner cannula 20 is shown and described as an inlet conduit designed to deliver blood to the pump 50 while the outer conduit is designed to transport blood away from the pump 50. It should be understood, however that the relative functions of the inner cannula and outlet conduit may be exchanged depending on the desired positions of the distal openings of the inner cannula 20 and outer conduit 30 and the direction of flow of blood by the pump 50.

Figure 6:
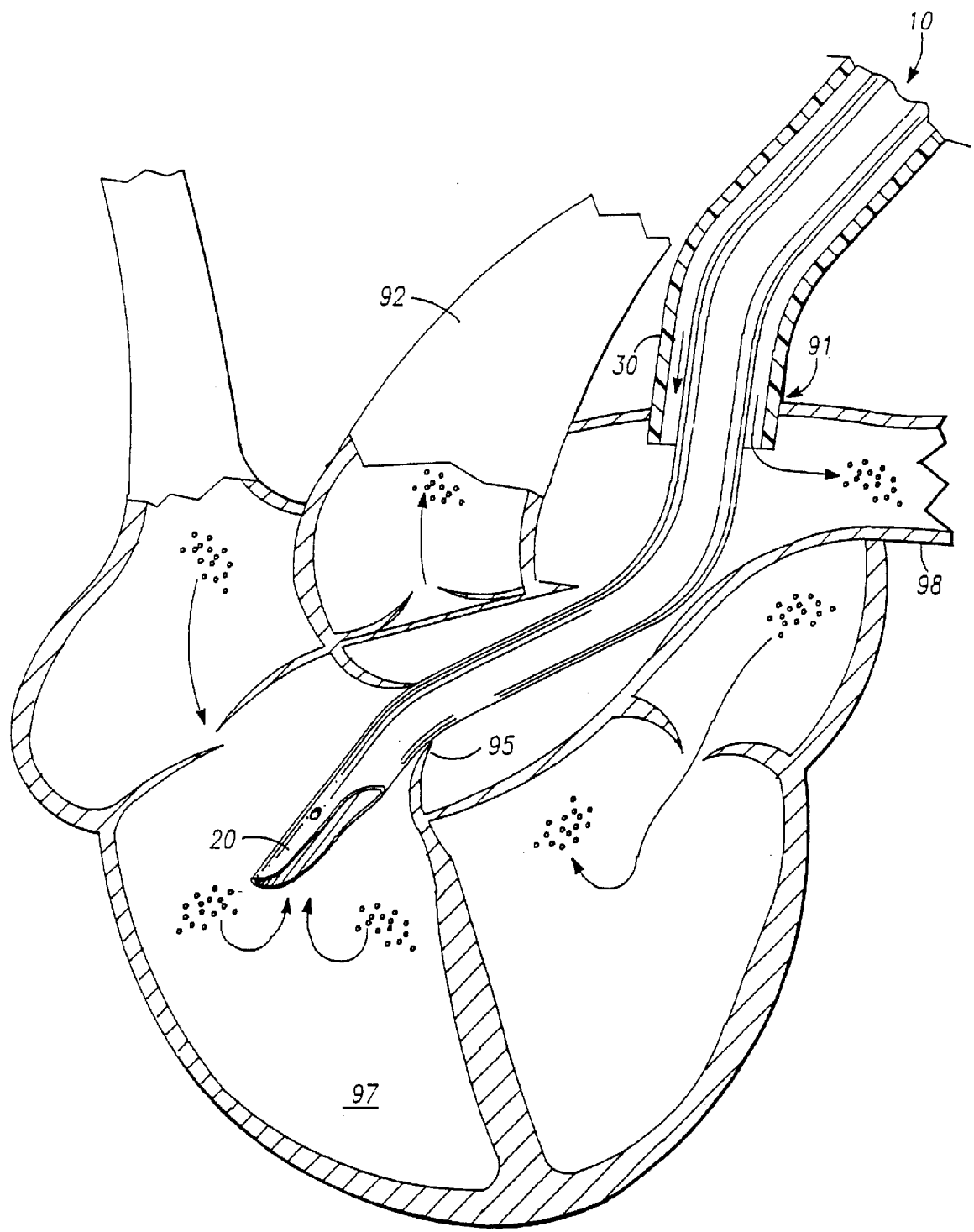
FIG. 6 is an illustration of the heart showing a portal formed in the pulmonary artery with the distal end of the outer conduit extending therethrought and the inner cannula being extending through the pulmonic valve and terminating in the right ventricle.

The inner cannula 20 has a distal opening 22 and a proximal opening 24. During use, the distal opening 22 is disposed in a major blood vessel, such as the aorta or in a right ventricle 97 as shown in FIG. 6. When blood enters the distal opening 22, it is transported through the inner cannula 20 to the pump 50. The pump 50 then forces the blood through the outer conduit 30 and downstream located blood vessel or chamber.

The inner cannula 20 is tubular and preferably made of flexible, bio-compatible material such as silicone, and reinforced with other material, such as steel wire, to provide sufficient radial stiffness to resist collapsing. The tip 25 of the inner cannula 20 is not reinforced and chambered to provide greater flexibility to improve advancement of the inner cannula 20 through small vessels or chambers and prevent trauma to surrounding tissue. Inner cannula 20 has a plurality of openings 27 formed near its tip 25 to allow blood to flow into the inner cannula 20 when the distal opening 22 is occluded. During use, a catheter or guide wire can also be extended through the openings 27 which enables the inner cannula 20 to be disposed at a desired location in the body. The inner cannula 20 can have a permanent bend formed therein curved 10 and 20 degrees to facilitate installation and removal from a blood vessel or chamber. The inner cannula 20 may also have radiopaque material added or printed on its surface of visibility when exposed to X-ray radiation.

The outer conduit 30 is tubular and made of flexible, bio-compatible material such as silicone, and reinforced with other material, such as steel wire, to provide sufficient radial stiffness to resist collapsing. The outer conduit 30 has a sufficient inside diameter so that the inner cannula 20 may be coaxially aligned therein and a blood flow passage 65 is created between the outside surface of the inner cannula 20 and the inside surface of the outer conduit 30. In the embodiment shown in FIG. 1, the distal opening 32 of the outer conduit 30 is extended through a portal 91 thereby creating a closed circuit between the inner cannula 20 and outer conduit 30. In the preferred embodiment, the outer conduit 30 is a an introducer, or a vascular graft, such as DACRON™ graft, or any other vascular graft available commercially and used for anastomoses.

The pump 50 is a reverse, axial flow, pump with coaxially aligned inlet and outlet ports formed therein. More specifically, pump 50 includes a rotor 70 axially aligned inside a cylindrical-shaped housing body 52. The rotor 70 is connected to a drive shaft 81 with is rotated at high speed by the driving unit 80. The distal opening of the housing body 52 is covered with a housing cap 60.

The housing cap 60 is preferably made from stainless steel or a rigid polymer with a plurality of outflow windows 64 formed therein. The outflow windows 64 are radially aligned around the inlet neck 62. The housing body 52 is cylindrical-shaped and includes a longitudinally aligned inlet tube 55. The inlet tube 55 is integrally attached at one end to the base plate 53 and includes a centrally aligned distal opening 56 and a plurality of radially aligned cut-outs 57. Disposed longitudinally inside the inlet tube 55 is the rotor 70. During operation, the rotor 70 is rotated which forces blood delivered to the inlet tube 55 through the cut-outs 57. The outside diameter of the inlet tube 55 is smaller than the inside diameter of the housing body 52 thereby creating a passageway 59 between the inlet tube 55 and the housing body 52. Attached over the distal opening of the housing body 52 is a housing cap 60. The housing cap 60 includes a circular base member 61 designed to attach tightly over the housing body 52. A cylindrical inlet neck 62 is perpendicular and centrally aligned on the base member 61. A plurality of outflow windows 64 are radially aligned on the base member 61 outside the inlet neck 62. The outer diameter of the inlet neck 62 is smaller then the inside diameter of the outer conduit 30 thereby creating a second passageway 65 for blood to flow through. The passageway 59 and the outflow windows 64 of the housing cap 60 are aligned when the housing cap 60 and the housing body 52 are assembled.

Figure 2:
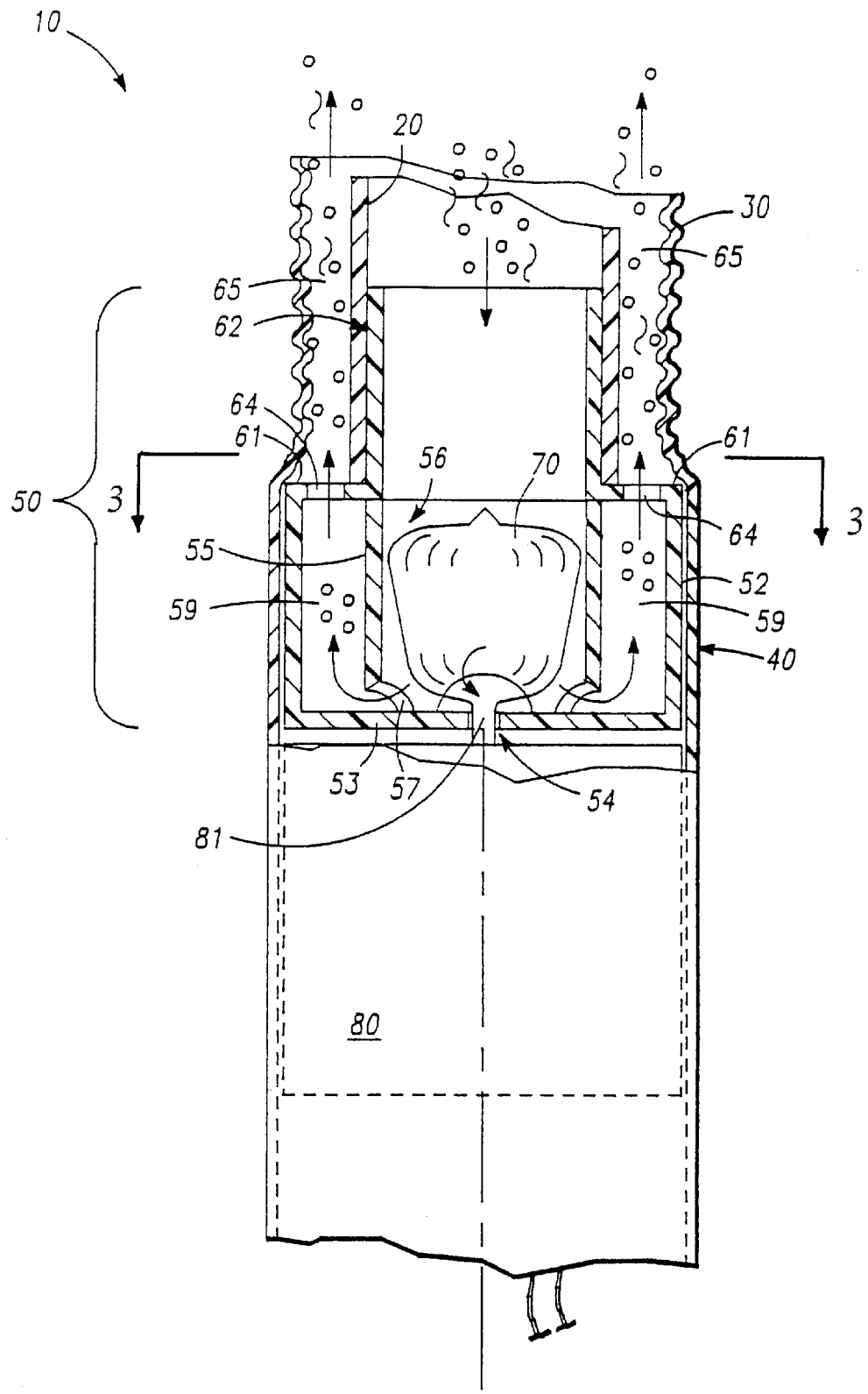
FIG. 2 is a side elevational view, partially in section, of the cardiac support apparatus.
Figure 3:
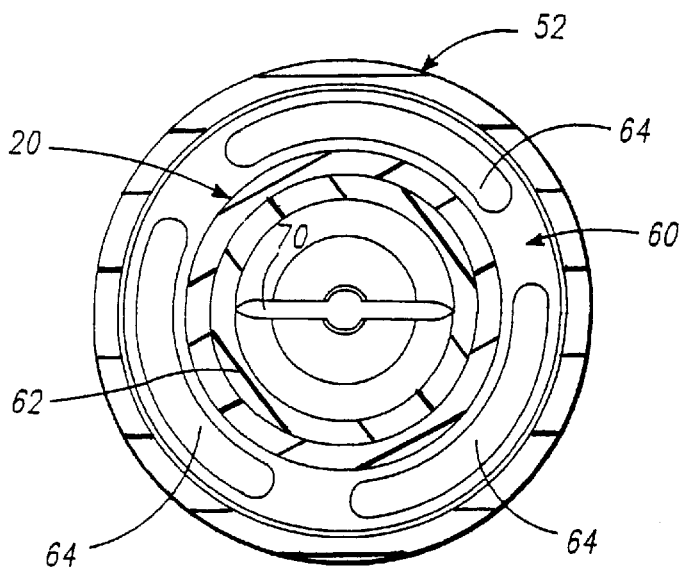
FIG. 3 is a sectional view of the apparatus taken along line 3—3 in FIG. 2.
Figure 4:
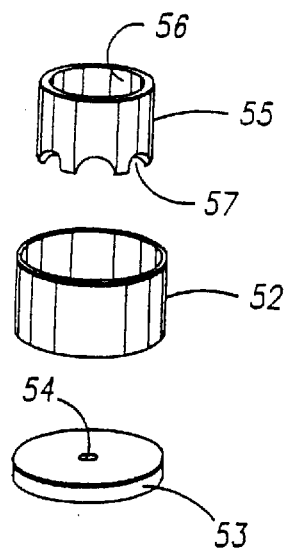
FIG. 4 is an exploded, perspective view of the pump's housing body with an inlet tube and base plate.
Figure 5:
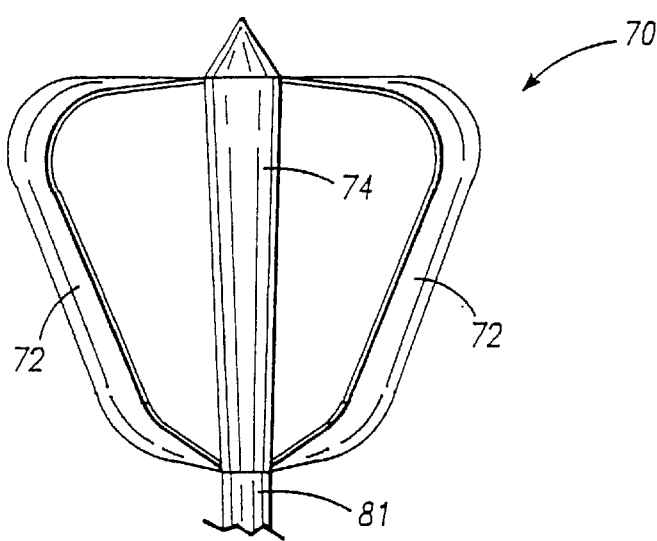
FIG. 5 is a side elevational view of the rotor.

As shown in FIGS. 2 and 5, the rotor 70 comprises one or multiple blades 72 extending from a longitudinally aligned central hub 74. The blades 72 are designed to lift blood along their proximal edge when the rotor 70 is rotated a range of specified speed.

Figure 1:
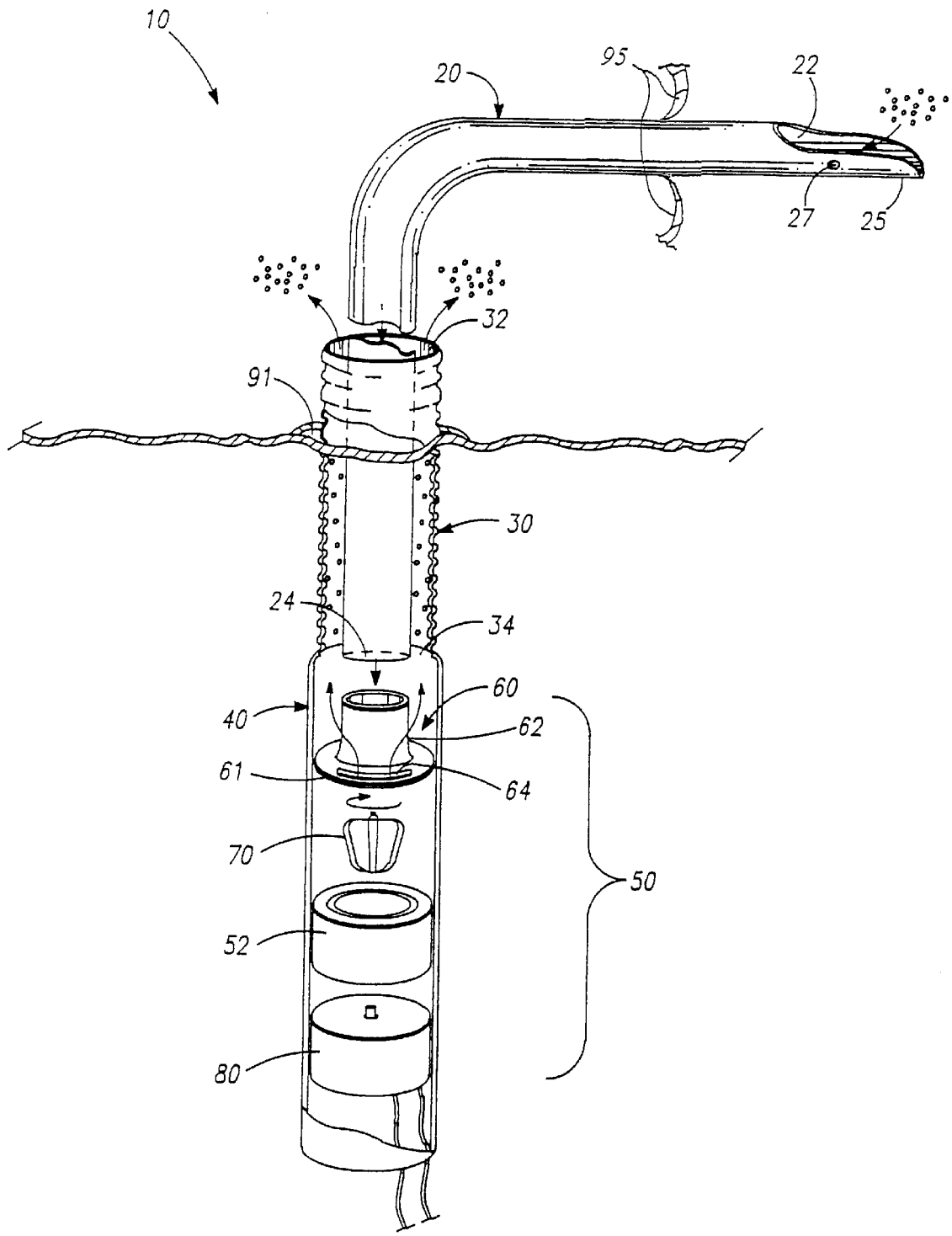
FIG. 1 is a perspective view, partially in section, of the cardiac support apparatus disclosed herein being installed through a portal formed in the major blood vessel with the distal opening of the outer conduit disposed just inside the portal and the inner cannula being disposed transvalvularly in a heart chamber.

As shown in FIGS. 1 and 2, the apparatus 10 is assembled in an optional elongated, cylindrical body 40 which connects to the proximal opening 34 of the outer conduit 30 designed to house the pump 50 and the drive unit 80. During use, the cylindrical body 40 acts as a handling means to enable the apparatus 10 to be placed in a desired location. In the other embodiments, not shown, the pump 50 may be sealed and attached to the outer conduit 30 with the drive unit 80 located externally.

During installation, the distal openings 22, 32, of the inner cannula 20 and outer conduit 30, respectively, are spaced apart and located in different blood vessels or on opposite sides of a heart valve thereby enabling blood to be pumped from one blood vessel or chamber to another. The inner cannula 20 and outer conduit 30 are coaxially aligned and have sufficient length so that only one portal opening is required into the major blood vessel or chamber.

The placement of the apparatus 10 requires the anastomoses of the distal end of the outer conduit to the sides of the targeted blood vessel or chamber using thoracoscopic suturing, or microstapling. Prior to suturing the outer conduit 30 to the blood vessel, the blood vessel can be isolated by using a "C" clamp or the use of thoracoscopic clamps best described in Evard, P. et al. in U.S. Pat. No. 5,425,705 or similar clamps capable of passing small ports on the patient's body and could isolate a section of a vessel without complete occlusion of the vessel in questions.

FIG. 6 is an illustration of the cardiac support apparatus 10 being used to provide cardiac support to the right side of the heart by pumping blood from the right ventricle 97 to the pulmonary artery 98. In this instance, a portal 91 is formed in the pulmonary artery 98 through which the distal end of the outer conduit 30 is extended. The inner cannula 20 is then inserted into the portal 91, through the pulmonic valve 95 and into the right ventricle 97.

Figure 7:
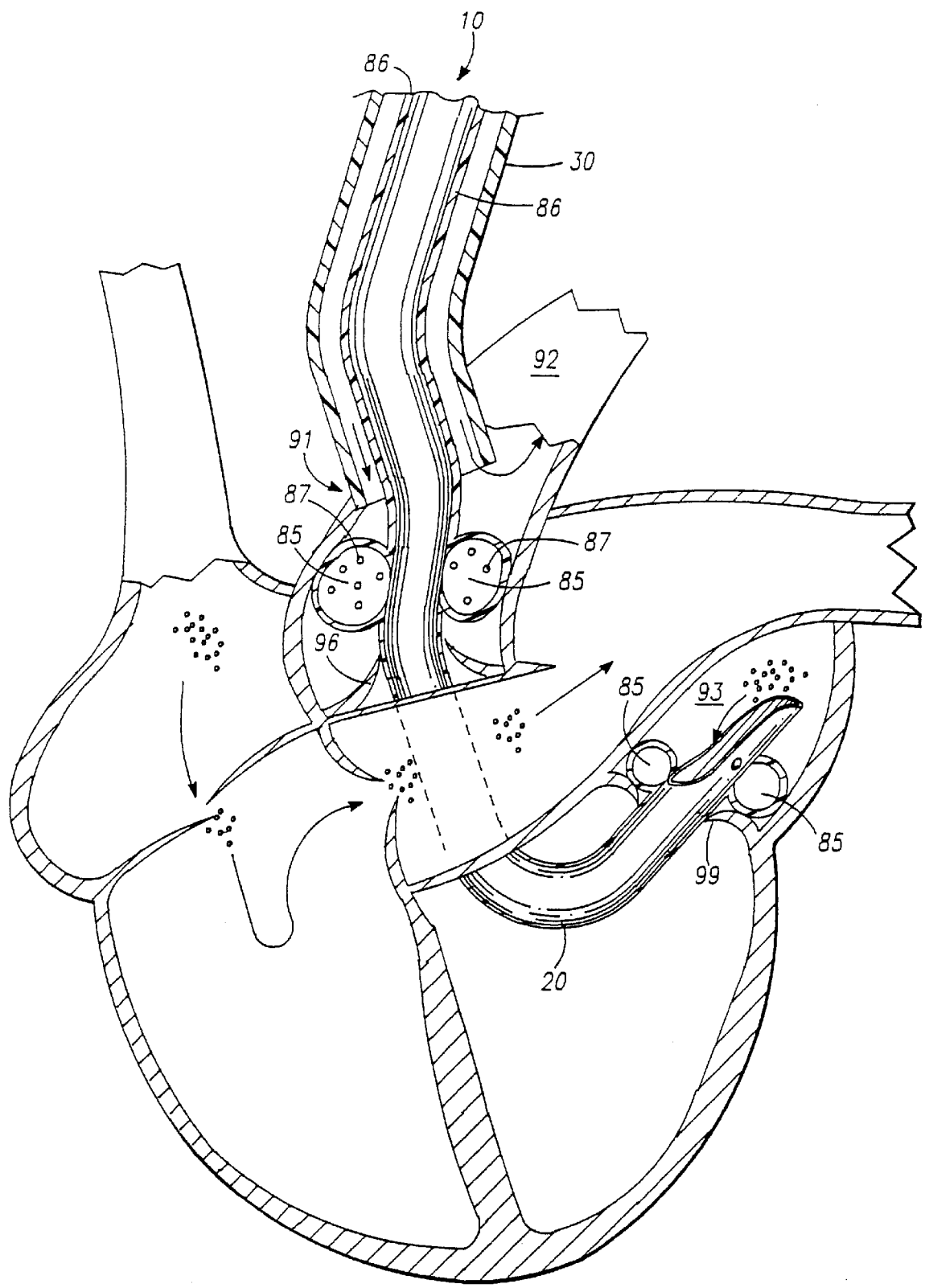
FIG. 7 is an illustration of the heart showing a portal formed in the aorta with the distal end of the outer conduit extending therethrough and the inner cannula being extended through the aortic valve, left ventricle, and mitral valve and terminating in the left atrium.

FIG. 7 is an illustration showing the apparatus 10 with the outlet conduit being attached to a portal 91 formed in the aorta 92 and the inner cannula 20 being extended through the portal 91, then the aortic and mitral valves 96, 99, respectively, and into the left atrium 93.

After the portal is created in the desired blood vessel, the outer conduit 30 is then inserted into the portal 91. A suture may be used to hold the outer conduit 30 inside the portal 91. A commercially available high stiffness guide wire may be passed through the outer conduit 30 to which the inlet cannula 20, and pump 50 are attached. The length of the outer conduit 30 must be sufficiently long to accommodate the pump 50. After placing the pump 50 in the outer conduit 30, the outer conduit 30 is filled with a saline solution, the pump 50 is primed if necessary, and air is completely removed from the pump 50 and the outer conduit 30. The driving unit 80 is then installed over the proximal end of the pump 50. A silicone plug must be used to seal the outer conduit 30 if the driving unit 80 located externally. After the installation is completed, the "C" clamp is released gradually and homeostasis at all possible bleeding sites are examined visually or with the aid of a viewing scope inserted into the body. Assuming acceptable homeostasis is achieved, then the "C" clamp 300 may be completely released but kept in position to clamp the anastomoses site in case of an emergency.

At this point, the guide wire can be advanced with the help of imaging techniques to dispose the distal end of the inlet cannula 20 in the desired blood vessel or heart chamber. While positioning the distal end of the inlet cannula 20, the pump may need to be advanced in the outlet conduit 30 by pushing the positioning rod into the outer conduit. A suture or a laproscopic clamping device may then be used to hold the apparatus in place. After securing the apparatus 10, the guide wire is removed from and the pump 50 is activated to initiate blood pumping.

After the pump 50 is activated, a drug known to slow or completely stop the heart can be administered as required. The pumping rate of the pump 50 is then adjusted to maintain sufficient circulation. The pumping rate can also be adjusted to accommodate changes in the circulatory demand. The pump 50 can also be equipped with means (not shown) for measuring the blood pressure, the presence of blood at the tip of the inner cannula, or other parameters that could indicate to the treating physician if a change in speed is required. Also, the apparatus 10 may include sensors (not shown) that sense the pressure at the proximal opening of the inner cannula 20, wherein a preset pressure change could signal the need to change the pumping capacity of apparatus 10. For example, when the pressure at the distal end of inner cannula 20 decreases by a certain increment, which indicate the commencement of pump suction, a controller used with the apparatus 10 could signal the user or automatically decrease the pump speed to return to a pre-selected pressure at the inner cannula 20.

To remove the apparatus 10, the suture or laproscopic clamping device is first disconnected enabling the apparatus 10 to move. The pump 50 is retracted through the outer conduit 30, the "C" clamp 300 is clamped, thoracoscopically the anastomoses is restored using common thoracoscopic techniques for suturing or stapling, then anastomoses is removed and the patient's skin wound is closed using know surgical techniques for wound closure.

Also, as shown in FIG. 7, an optional balloon 85 may be disposed on the outside surface of the inner cannula 20 to seal, or to deliver a cool fluid or mediation to the adjacent tissue. The balloon 85 is disposed around the inner cannula 20 and connected to a conduit 86 through which air, or a suitable coolant, or mediation may be transported to the balloon 85. When the balloon 85 is used to deliver medication, a plurality of perforations 87 may be formed on the surface of the balloon 85 to allow medication to be delivered to the surrounding tissue.

Using the above described apparatus, a method of providing cardiac support is also provided which includes the following steps:

a. selecting a blood flow support apparatus including coaxially aligned inner cannula and outlet conduit and a coaxially aligned, reverse flow pumping means disposed therebetween, said pumping means capable of pumping blood through a body;

b. forming a portal in a blood vessel connected to the heart;

c. connecting said outer conduit through said portal;

d. inserting said inner cannula through said portal so that said distal opening on said inner cannula is disposed proximal and distally, respectively, on opposite sides of a desired heart valve, and;

e. activating said pumping means so that blood adjacent to said distal opening on said inner cannula is pumped through said inner cannula to said outer conduit.

In compliance with the statute, the invention, described herein, has been described in language more or less specific as to structural features. It should be understood, however, the invention is not limited to the specific features shown, since the means and construction shown comprised only the preferred embodiments for putting the invention into effect. The invention is, therefore, claimed in any of its forms or modifications within the legitimate and valid scope of the amended claims, appropriately interpreted in accordance with the doctrine of equivalents.

I claim:

1. A dual lumen cannula, comprising:

a pair of generally concentric conduits formed of biocompatible material, each of said conduits having a proximal end and a distal end, said distal ends being disposed a distance from one another; and wherein said proximal ends are communicatively coupled together such that a fluid may be simultaneously transported in a first direction within one of said conduits and in a generally reverse direction within the other of said conduits.

2. The dual lumen cannula as recited in claim 1, wherein said pair of conduits comprises an inner cannula disposed generally concentrically within an outer cannula.

3. The dual lumen cannula as recited in claim 2, wherein said distal end of said outer cannula is dimensioned for insertion through a portal formed in one of a pulmonary artery and an aorta connected to a heart.

4. The dual lumen cannula as recited in claim 2 wherein inner cannula further includes material responsive to X-ray radiation.

5. The dual lumen cannula as recited in claim 2 wherein said distal end of said inner cannula includes a flexible tip.

6. The dual lumen cannula as recited in claim 2 wherein said inner cannula is formed with a permanent bend to facilitate installation and positioning of said inner cannula.

7. The dual lumen cannula as recited in claim 2 wherein said outer cannula is a vascular graft.

8. A dual lumen cannula, comprising:

an inner cannula disposed generally concentrically within an outer cannula, each of said inner and outer cannulas formed of biocompatible material and having a proximal end and a distal end, said distal ends being disposed a distance from one another;

wherein said proximal ends are communicatively coupled together such that a fluid may be simultaneously transported in a first direction within said inner cannula and in a generally reverse direction within said outer cannula; and wherein said distal end of said inner cannula includes a plurality of openings to further allow transport of fluid to or from said inner cannula.

9. A dual lumen cannula, comprising:

a first conduit formed of biocompatible material having a lumen extending between a distal end and a proximal end;

a second conduit formed of biocompatible material having a lumen extending between a distal end and a proximal end, said distal end of said second conduit dimensioned for insertion through a portal formed in a vessel connected to a heart;

said first conduit disposed generally concentrically within said second conduit and positioned such that said distal end of said first conduit extends past said distal end of said second conduit; and wherein said proximal ends of said first and second conduits are communicatively coupled to provide a simultaneous reverse flow of fluid between said first and second conduits.

10. The dual lumen cannula as recited in claim 9 wherein said portal is formed in one of a pulmonary artery and an aorta connected to said heart.

11. The dual lumen cannula as recited in claim 9 wherein said first conduit includes a radiopaque material for visualization from an exterior of the body.

12. The dual lumen cannula as recited in claim 9 wherein said distal end of said first conduit includes a flexible tip.

13. The dual lumen cannula as recited in claim 9 wherein said distal end of said first conduit includes a plurality of openings to further allow transport of fluid into said first conduit.

14. The dual lumen cannula as recited in claim 9 wherein said first conduit is formed with a permanent bend to facilitate installation and positioning of said first cannula.

15. The dual lumen cannula as recited in claim 9 wherein said proximal ends of said first and second conduits are coupled to a pumping system capable of creating an outflow of blood from said heart through said lumen of said first conduit and an inflow of blood into said vessel connected to said heart through said lumen of said second conduit.

16. The dual lumen cannula as recited in claim 15 wherein said pumping system comprises a reverse flow pump.

17. A dual lumen cannula comprising:

a first conduit formed of biocompatible material disposed generally concentrically within a second conduit formed of biocompatible material such that a distal end of said first conduit extends past a distal end of said second conduit, said distal end of said second conduit dimensioned for introduction through a portal formed in a vessel connected to a heart; and each of said first and second conduits including proximal ends communicatively coupled together to provide a simultaneous reverse flow of blood through said first and second conduits.

18. The dual lumen cannula as recited in claim 17, wherein the simultaneous reverse flow of blood through said first and second conduits is provided by a pump apparatus coupled between said proximal ends of said first and second conduits.

19. The dual lumen cannula as recited in claim 18, wherein said pump apparatus comprises a reverse flow pump.

* * * * *

UNITED STATES PATENT AND TRADEMARK OFFICE
CERTIFICATE OF CORRECTION

PATENT : 6,123,725
DATED : September 26, 2000
INVENTOR(S) : Walid N. Aboul-Hosn

It is certified that error appears in the above-identified patent and that said Letters Patent is hereby corrected as shown below:

Column 6, line 38 (Claim 1, line 3), insert --and being movably displaceable relative to one another-- following the word "material";

Column 7, lines 1-2 (Claim 8, line 5-6), cancel "being disposed a distance from" and insert --being movably displaceable relative to-- therefor;

Column 7, line 21 (Claim 9, line 10), insert --and being movably displaceable with-- following the word "within"; and Column 8, line 18 (Claim 17, line 4), insert --, said first and second conduits being movably displaceable relative to one another-- following the word "material".

Signed and Sealed this

Thirty-first Day of October, 2000

Attest:

Q. TODD DICKINSON

*Attesting Officer*  *Director of Patents and Trademarks*